(12) United States Patent
Wagner et al.

(10) Patent No.: US 9,183,732 B2
(45) Date of Patent: Nov. 10, 2015

(54) DUAL BAND NURSE CALL SYSTEM

(71) Applicant: Tektone Sound & Signal Mfg., Inc., Franklin, NC (US)

(72) Inventors: Henry N. Wagner, Cedarburg, WI (US); David Neperud, Grafton, WI (US); Scott Lederer, Verona, WI (US); William Steinike, Cedarburg, WI (US)

(73) Assignee: Tektone Sound & Signal Mfg., Inc., Franklin, NC (US)

( * ) Notice: Subject to any disclaimer, the term of this patent is extended or adjusted under 35 U.S.C. 154(b) by 16 days.

(21) Appl. No.: 13/961,654

(22) Filed: Aug. 7, 2013

(65) Prior Publication Data

US 2014/0043150 A1 Feb. 13, 2014

Related U.S. Application Data

(60) Provisional application No. 61/680,578, filed on Aug. 7, 2012.

(51) Int. Cl.
| | |
|---|---|
| *G08B 25/14* | (2006.01) |
| *G08B 25/10* | (2006.01) |
| *A61B 5/00* | (2006.01) |
| *H04B 1/713* | (2011.01) |
| *G08B 25/00* | (2006.01) |
| *H04B 7/155* | (2006.01) |
| *H04W 76/02* | (2009.01) |

(52) U.S. Cl.
CPC .............. *G08B 25/10* (2013.01); *A61B 5/7465* (2013.01); *G08B 25/009* (2013.01); *H04B 1/713* (2013.01); *A61B 2560/00* (2013.01); *H04B 7/155* (2013.01); *H04W 76/02* (2013.01)

(58) Field of Classification Search
CPC .................................... A61B 2560/00
USPC ............. 340/286.01, 286.07, 539.11, 539.12, 340/539.16, 539.17, 7.25, 7.28; 455/12.1, 455/41.2, 423, 428, 552.1, 553.1
See application file for complete search history.

(56) References Cited

U.S. PATENT DOCUMENTS

| | | | |
|---|---|---|---|
| 5,319,355 A | 6/1994 | Russek | |
| 5,319,363 A | 6/1994 | Welch et al. | |
| 5,561,412 A | 10/1996 | Novak et al. | |
| 5,699,038 A | 12/1997 | Ulrich et al. | |
| 8,064,412 B2 * | 11/2011 | Petite | 370/338 |
| 2007/0155318 A1 * | 7/2007 | Monte et al. | 455/12.1 |
| 2007/0243822 A1 * | 10/2007 | Monte et al. | 455/12.1 |
| 2009/0088605 A1 * | 4/2009 | Ross et al. | 600/300 |
| 2011/0111700 A1 * | 5/2011 | Hackett | 455/41.2 |
| 2012/0092154 A1 * | 4/2012 | Petite | 340/539.1 |

* cited by examiner

*Primary Examiner* — Van Trieu
(74) *Attorney, Agent, or Firm* — McHale & Slavin, P.A.

(57) ABSTRACT

A nurse call station and system capable of scalable accommodating a plurality of wireless nodes by incorporating a dual band of 900 MHz and 2.4 GHz for use in transmission and repeating an identification signal. The nurse call system is comprised of various components that includes but is not limited to gateway nodes, transmitter nodes, repeaters, end nodes and locators. Transmitter nodes may be comprised of various transmitter styles including wireless check in stations, wireless emergency call stations and resident bed stations.

18 Claims, 17 Drawing Sheets

| OPERATING MODE | DESCRIPTION | USAGE |
|---|---|---|
| OMODE_INVALID | INVALID OPERATING MODE, PLACEHOLDER FOR MISCONFIGURED STATES | DEFAULT OPERATING MODE CONFIGURED ON STARTUP UNTIL THE CONFIGURATION DATA IS LOADED |
| OMODE_UNMANAGED | THE UD IS IN AN UNMANAGED STATE. THIS INDICATES IT DOES NOT BELONG TO AN NCS NETWORK (HAS NOT BEEN COMMISSIONED OR REGISTERED) | UPON FACTORY RESET, THE UD WILL CLEAR ITS CONFIGURED SHORT ADDRESS AND BEGIN SENDING PERIODIC "COMMISSIONING REQUEST" MESSAGES |
| OMODE_COMMISSIONED | THIS UD HAS BEEN COMMISSIONED BY A PNCS (ASSIGNED A SHORT ADDRESS) BUT HAS NOT COMPLETED THE REGISTRATON PROCESS | ONCE A COMMISSIONING ACK HAS BEEN RECEIVED, A SHORT ADDRESS IS ASSIGNED AND PERIODIC "REGISTRATION REQUEST" MESSAGES BEGIN |
| OMODE_MANAGED | THE UD HAS BEEN REGISTERED BY A PNCS (ASSIGNED A SHORT ADDRESS AND DEVICE TYPE CONFIRMED) | IN THE STATE, THE UD SENDS PERIODIC SUPERVISORY MESSAGES INDICATING ITS PRESENCE ON THE NCS NETWORK |
| OMODE_TEST | THIS MODE IS INTENDED FOR USE WHEN INTERACTING WITH THE UD VIA DIAGNOSTIC COMMAND LINE INTERFACE | IN THIS STATE, THE UD DOES NOT SEND ITS PERIODIC SUPERVISORY MESSAGES |
| OMODE_FACTORING_RESET_PENDING | A FACTORY RESET HAS BEEN INITIATED BUT HAS NOT YET COMPLETED | AT POWER UP, IF THE COMMISSIONING BUTTON IS HELD FOR 5 SECONDS, A FACTORY RESET IS INITIATED. THIS CLEARS THE COMMISSIONING DATA AND PLACES THE UD INTO AN UNMANAGED STATE |
| OMODE_HIGH_LOAD_SIMULATION | THE UD IS PERFORMING A HIGH LOAD SIMULATION TEST | IF A HIGH LOAD SIMULATION TEST IS STARTED, THE UD CONTINUOUSLY UPDATES THE STATE OF MULTIPLE SIMULATED NODES |
| OMODE_MAX | INVALID MODE | USED AS A BOUNDS CHECK FOR THE VALID OPERATING MODES |

*FIG. 5*

| DESCRIPTION | NC/NO | TOGGLE CONFIG | INPUT HIGH | INPUT LOW | RISING EDGE | FALLING EDGE |
|---|---|---|---|---|---|---|
| NORMALLY OPEN, TRIGGER ON CLOSED | | | IDLE | IDLE | IDLE | SEND MESSAGE |
| NORMALLY OPEN, TRIGGER ON OPEN AND CLOSE | | X | IDLE | IDLE | SEND MESSAGE | SEND MESSAGE |
| NORMALLY CLOSED, TRIGGER ON OPEN | X | | IDLE | IDLE | SEND MESSAGE | IDLE |
| NORMALLY CLOSED, TRIGGER ON OPEN AND CLOSE | X | X | IDLE | IDLE | SEND MESSAGE | SEND MESSAGE |

*FIG. 6*

| APPLICATION SPECIFIC PIN NAME | CONSTANTS | MCU PORT | HARDWARE INTERFACE |
|---|---|---|---|
| NC/NO CONFIG PIN 0 | STATION_NCNO0_* | P1.6 | J6, PINS 1-2 |
| NC/NO CONFIG PIN 1 | STATION_NCNO1_* | P1.7 | J6, PINS 3-4 |
| NC/NO CONFIG PIN 2 | STATION_NCNO2_* | P2.4 | N/A, HARD-WIRED TO GND |
| NC/NO CONFIG PIN 3 | STATION_NCNO3_* | P2.5 | J6, PINS 5-6 |

*FIG. 7*

| APPLICATION SPECIFIC PIN NAME | CONSTANTS | MCU PORT | HARDWARE INTERFACE |
|---|---|---|---|
| TOGGLE CONFIG PIN 0 | STATION_TOGGLE0_* | P4.6 | J7, PINS 1-2 |
| TOGGLE CONFIG PIN 1 | STATION_TOGGLE1_* | P.7 | J7, PINS 3-4 |
| TOGGLE CONFIG PIN 2 | STATION_TOGGLE2_* | P6.2 | N/A, HARD-WIRED TO GND |
| TOGGLE CONFIG PIN 3 | STATION_TOGGLE3_* | P6.3 | J7, PINS 5-6 |

*FIG. 8*

| APPLICATION SPECIFIC PIN NAME | CONSTANTS | MCU PORT | HARDWARE INTERFACE |
|---|---|---|---|
| STATION OUTPUT PIN 0 | STATION_OUTPUT0_* | P4.0 | N/A, HARD-WIRED TO LED D2 |
| STATION OUTPUT PIN 1 | STATION_OUTPUT1_* | P4.1 | J3, PINS 5 |
| STATION OUTPUT PIN 2 | STATION_OUTPUT2_* | P4.2 | J3, PINS 6 |

*FIG. 9*

| APPLICATION SPECIFIC PIN NAME | CONSTANTS | MCU PORT | HARDWARE INTERFACE |
|---|---|---|---|
| STATION INPUT PIN 0 | STATION_INPUT0_* | P2.0 | J3, PINS 2 |
| STATION INPUT PIN 1 | STATION_INPUT1_* | P2.1 | J3, PINS 3 |
| STATION INPUT PIN 2 | STATION_INPUT2_* | P2.2 | N/A, HARD-WIRED TO TAMPER SW |
| STATION INPUT PIN 3 | STATION_INPUT3_* | P2.3 | J3, PINS 4 |

*FIG. 10*

DUAL BAND NURSE CALL SYSTEM

PRIORITY CLAIM

In accordance with 37 C.F.R. 1.76, a claim of priority is included in an Application Data Sheet filed concurrently herewith. Accordingly, the present invention claims priority to U.S. Provisional Patent Application No. 61/680,578, entitled "DUAL BAND NURSE CALL SYSTEM", filed Aug. 7, 2012. The contents of which the above referenced application is incorporated herein by reference.

FIELD OF THE INVENTION

This invention relates to the emergency/nurse communication field and more particularly to a dual band call system.

BACKGROUND OF THE INVENTION

Hospitals, assisted living, and independent living facilities exist to provide health care for their patients and/or residents. The health care providers must remain vigilant and timely respond to patients under varying conditions. Communication devices common to such facilities are commonly referred to as nurse call or emergency call systems. The call systems provide a convenient and effective method of signaling health care providers when patient assistance is requested in both emergency and non-emergency events.

Nurse call systems are intended for use by residents that are ambulatory, as opposed to those confined to a bed. Current systems are hardwired, wireless and telephone based technologies. In some instances a wireless technology is most advantageous but due to building layout and/or materials of construction may not provide a strong communication signal. Conventional call systems are limited in capacity due to radio frequency limitations.

Common to such systems is the need for the communication system to provide reliable call initiation from resident areas and subsequent annunciation to a central location, such as a staff control room. Equipment in hospitals and other healthcare facilities sometimes communicate the status of the equipment via a network to a computer located at a nurse station or other location in the facility. If an alarm condition is detected, some sort of notification of the condition causing the alarm is shown on the display screen of the computer. U.S. Pat. No. 5,319,363 discloses a number of different patient care devices provide information to a workstation at a nurse's station. U.S. Pat. Nos. 5,561,412 and 5,699,038 discloses how hospital beds can be used to communicate information via a network to a computer at a nurse's station.

Health care employees may also wear or carry pendants that communicate wirelessly with a network within the healthcare facility. Information from the badges, and from receivers with which the badges communicate, can be used to determine the location of an individual in the healthcare facility.

Should a health care provider notice that an alarm condition exists from a master controller, the provider assigned to a patient associated with the alarm condition may attend to the alarm condition.

U.S. Pat. No. 5,319,355 discloses a system in which alarm conditions detected by various pieces of equipment are transmitted to a master alarm control which then automatically communicates information about all received alarm conditions carried by designated caregivers.

What is needed in the industry is a call system that will allow multiple connections to a central location without a loss of signal by use of a low power 900 MHz frequency for pendant operation and high power 2.4 GHz from a remote location for advancing of a signal without degradation.

SUMMARY OF THE INVENTION

The instant invention addresses the above identified limitation by providing a nurse call system employing a dual frequency/hybrid approach.

The dual frequency/hybrid approach maximizes the messaging throughput yet will conserve battery life in the use of transmitting pendants and universal devices. A pendant transmitting device communicates over a 900 MHz, IEEE 802.15.4 compliant radio link to a repeater. The repeater then relays the message to a USB gateway over a 2.4 GHz IEEE 802.15.4 compliant radio link.

The nurse call system includes, but is not limited to, gateway nodes, transmitter nodes, repeaters and locators. Transmitter nodes may be comprised of various transmitter styles including wireless check in stations, wireless emergency call stations and resident bed stations. The various transmitter styles may be worn as a pendant, as well as mounted to a wall, ceiling, bed or the like. Alternatively, the transmitter style may include a handheld portable device in a universal form.

Accordingly, it is an objective of the instant invention to provide a dual frequency/hybrid approach that maximizes the messaging throughput while conserving battery life of the transmitter node when used in a pendant configuration.

An objective of the instant invention to provide a dual frequency/hybrid approach to improve the throughput and capacity of a network configuration.

It is a further objective of the instant invention to provide a nurse call system that operates in the frequency range of 900 MHz, IEEE 802.15.4 compliant radio link to a repeater. The repeater then relays the message to a USB gateway over a 2.4 GHz IEEE 802.15.4 compliant radio link wherein the 802.15.4 radio is based on a direct sequence spread spectrum ("DSSS") protocol.

It is yet another objective of the instant invention to provide a nurse call system that automatically changes frequencies to mitigate potential interference.

It is a still further objective of the invention to provide a nurse call system that may accommodate additional nodes by setting a configuration bit during individual node programming. In an additional configuration, the nurse call system may be configured for sending a message to an end node over a high speed link. An exemplary purpose of this high speed link includes a message for turning on/off a light.

It is a further objective of the instant invention to provide a transmitter node that is a universal radio module unit for use with the nurse call system that will incorporate two antenna configurations.

Other objectives and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

BRIEF DESCRIPTION OF THE FIGURES

FIG. 5 is table diagram of operating modes;

FIG. 6 is table of NC/NO/Toggle configuration input trigger behavior;

FIG. 7 is table depicting NC/NO Configuration Interface;

FIG. 8 sets for the toggle configuration jumpers;

FIG. 9 depicts station outputs;

FIG. 10 is a table representing station inputs;

DETAILED DESCRIPTION OF THE INVENTION

Figure 1:
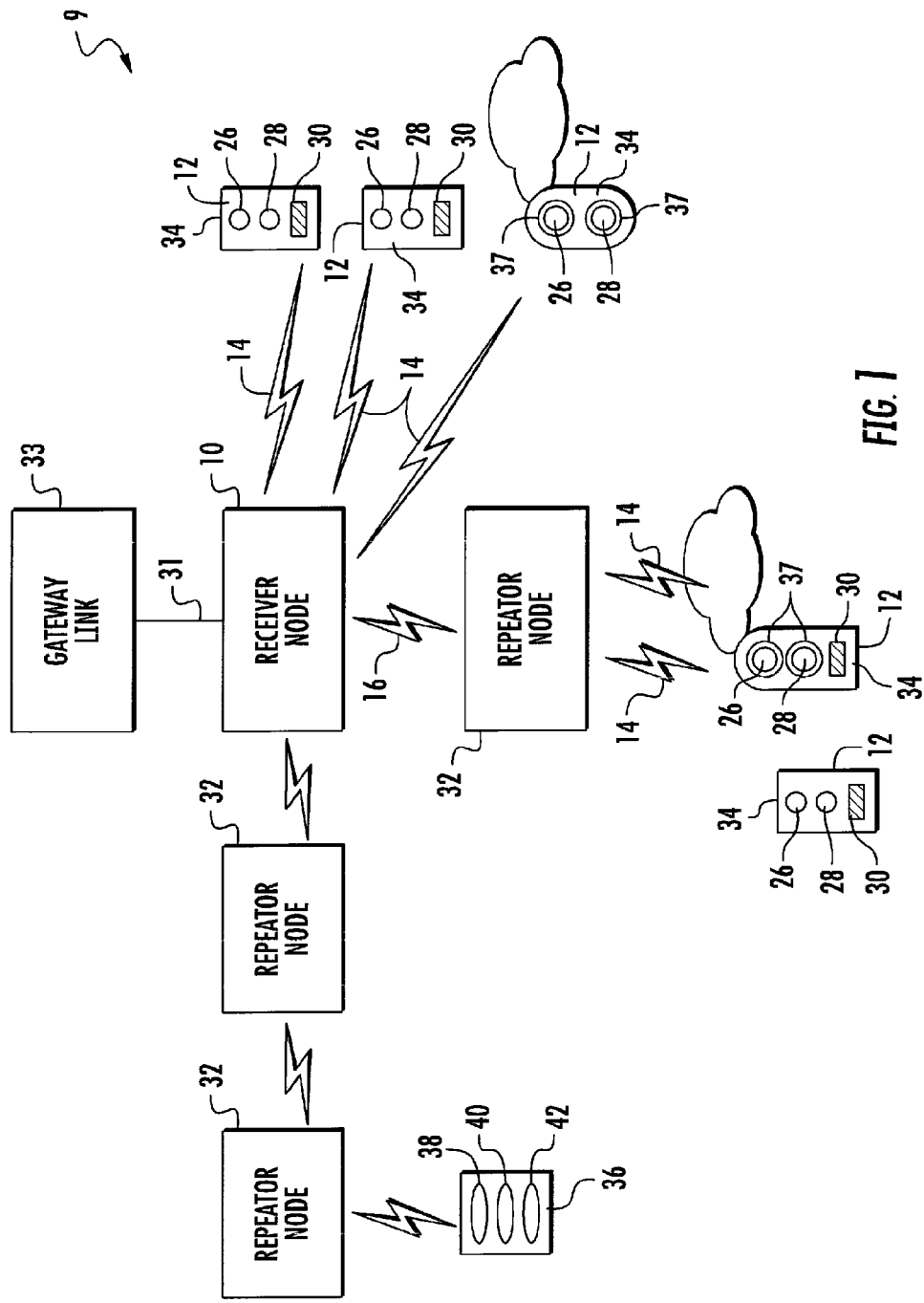
FIG. 1 is a block diagram schematically illustrating a nurse call system in accordance with the principles of the instant invention.

In accordance with FIG. 1, in a preferred embodiment, the nurse call system 9 of the instant invention comprises a receiver node 10 that is constructed and arranged to receive a radio signal from a plurality of transmitter nodes 12, such a pendant. The transmitter nodes 12 utilize a 900 MHz DSSS radio sub-system using an asynchronous frequency hopping scheme, which allows for extended RF range and allows for inherent frequency agility. A repeater 32 includes a receiver to accept identification signals from the transmitter nodes, the repeater 32 transferring the identification signals by 2.4 GHz. A locator is constructed and arranged to receive emergency and location messages from the transmitter nodes and send to the nearest repeater configured with LQI and RSSI data. The locator communicates with the repeaters at 900 MHz. The pendant is configured for low power sleep mode with periodic wakeups for supervisory messaging and ACK processing. The universal device, which is defined as a carrier board with configurable inputs/outputs and normally closed/normally open/toggle configuration jumpers. The universal device participates in the 900 MHz portion of the nurse call station providing a generic interface to trigger calls and respond to asynchronous messages based upon the configuration of the pins in the device. Nurse call and emergency call systems may be used interchangeably in this description.

In an exemplary embodiment, the transmitter node 12 includes a housing 34 made of plastic or other suitable materials and at least one depressible button 26. Preferably, each transmitter node 12 shall have two depressible buttons 26 and 28. Depression of at least one button 26 and 28 shall send an identification signal to the receiver node 10 via the repeater 32. The identification signal may be most any type of communication, preferably a person's voice or the signal may be a warning sound. Such identification signal may be audibly or visually output to a nurse station.

Figure 13A:
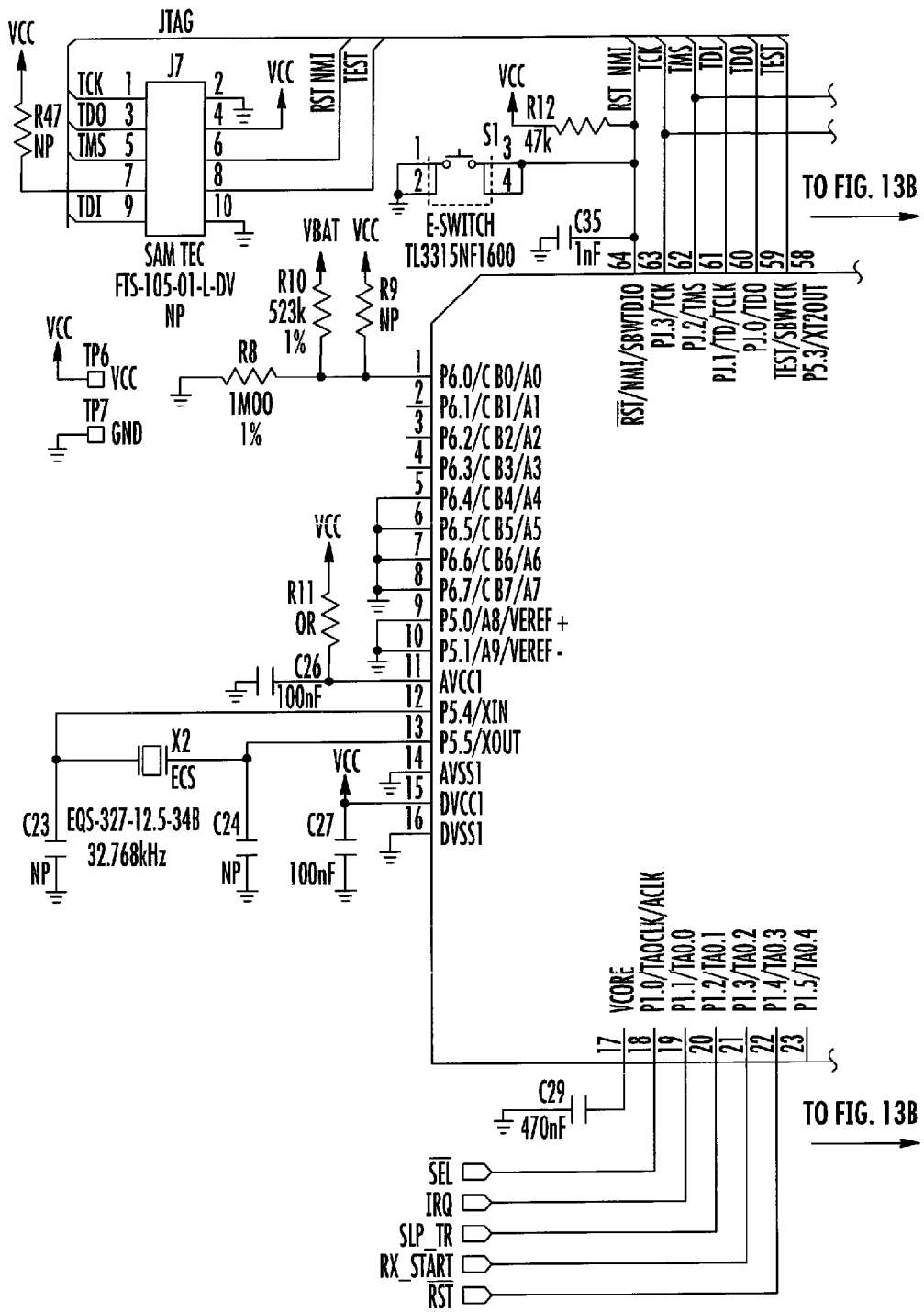
FIGS. 13A-13B illustrate a pendant schematic.
Figure 13B:
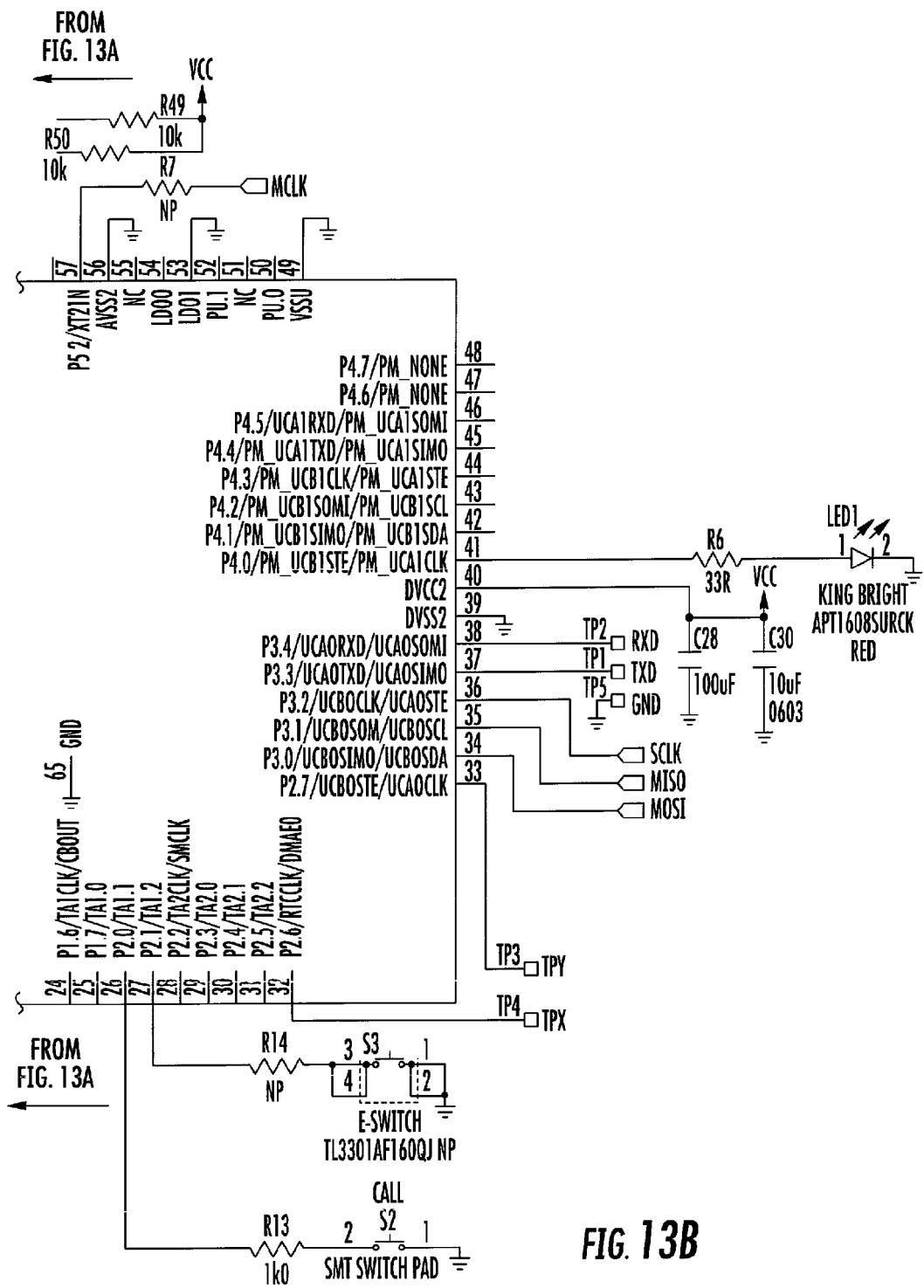
Figure 14A:
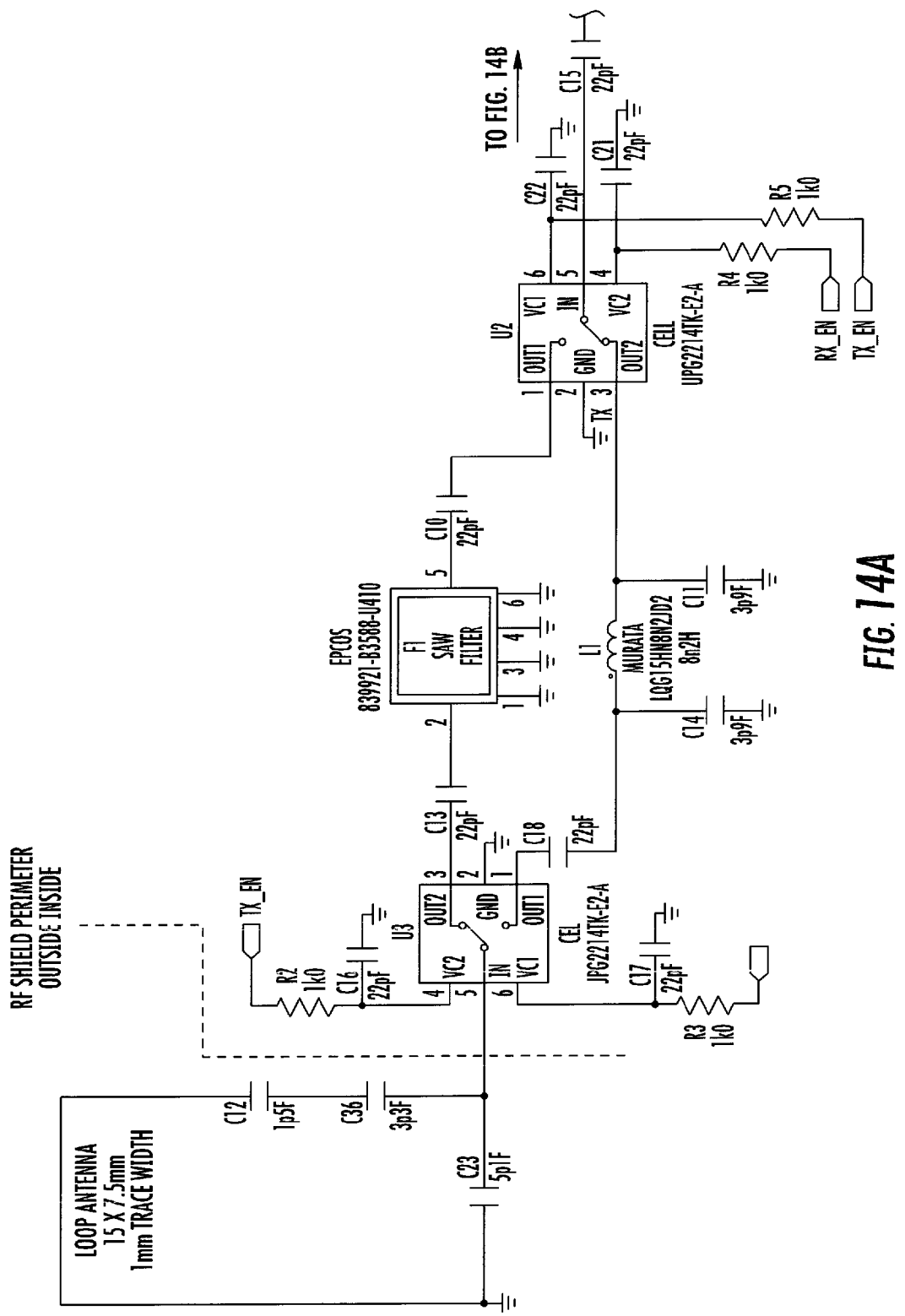
FIGS. 14A-14B illustrate a pendant transceiver schematic.
Figure 14B:
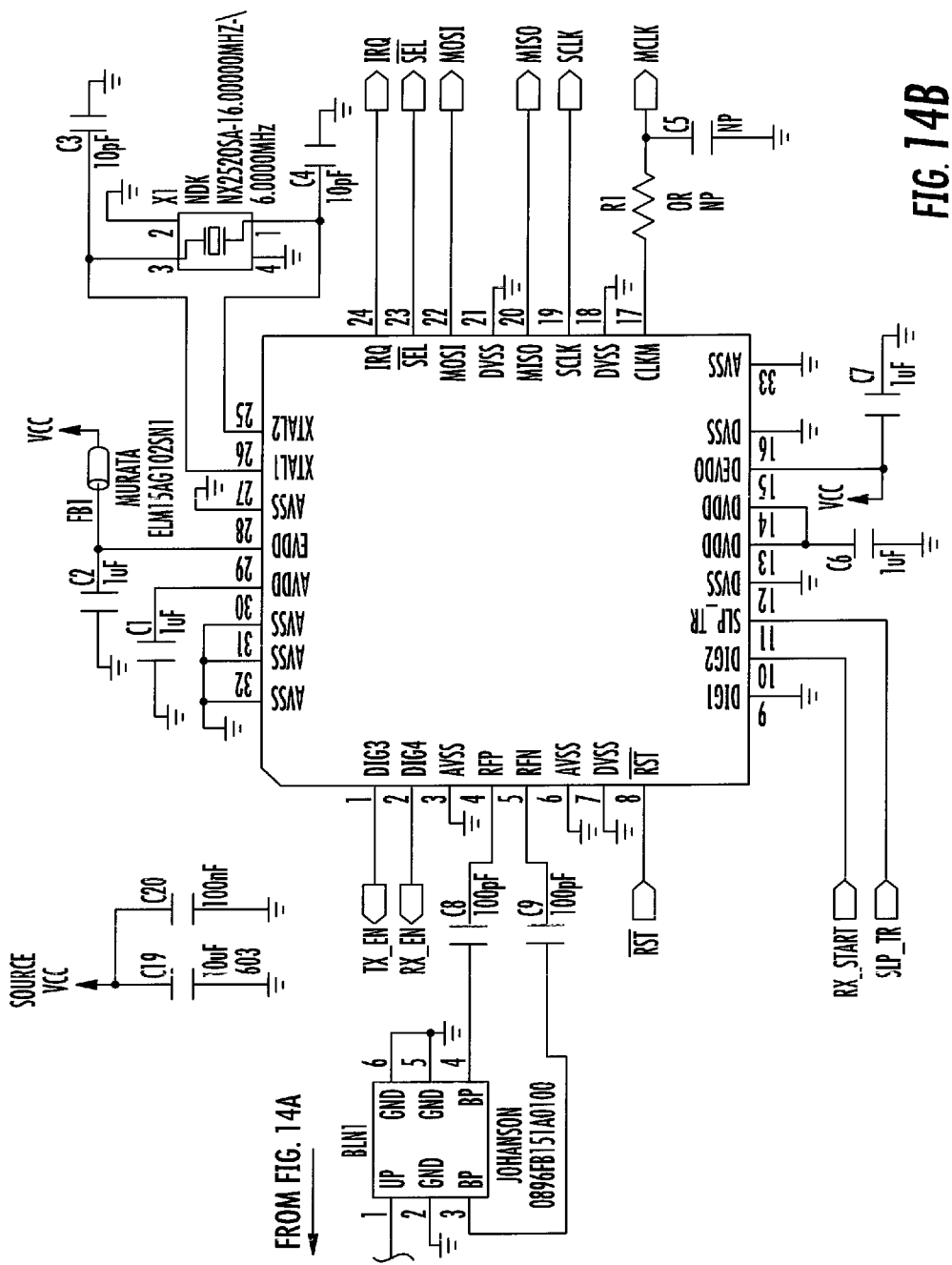

A typical installation consists of sub-networks. Each sub-network is comprised of a dual frequency radio system consisting of a low power 900 MHz system for the end device to repeater node 32, and a higher power 2.4 GHz system for the repeater node 32 to the receiver node 10 which can be hard wired 31 to a gateway link 33. The transmitter nodes 12 may always enter a low power mode whenever it is not communicating, the reduced power consumption is advantageous since the transmitter nodes are often powered by low-capacity, small size batteries such as lithium coin cell batteries. The frequency hopping protocol allows the nodes to remain in their lower power mode for relatively long periods of time to enhance battery life and dependability. The receiver node 10 may be used to transmit a message to an end node 36. The end node 36 may be constructed and arranged to alert a nurse or other aide of an event. The end node 36 may be a pocket pager, PDA or other similar alerting device. The end node 36 may include lights 38, 40 and 42 to visually indicate an event. The pendant is based upon an ultra low power microcontroller having a 16-bit RISC CPU architecture, 16-bit registers, and constant generators. A digitally controlled oscillator allows the microcontroller to instantly wake from a low power mode. The microcontroller configuration is with a 3.3-V LDO and a 10 bit analog to digital converter, FIGS. 13A-13B. A universal serial communication interface (USCI) allows coupling. The microcontroller is coupled to a switch pad for making calls. FIGS. 14A-14B disclose the pendant controller 900 MHz transceiver and relays coupled to a loop antenna. The transceiver supports a radio interface between the antenna and the microcontroller. The circuit provides an analog radio, digital modulation and demodulation, including time and frequency synchronization, as well as data buffering.

The housing may additionally include a light 37, preferably an LED that activates upon depression of at least one button 26 and 28. After depressing at least one button 26 and 28, the transmitter node 12 may be reset by multi-button depression. The light 37 about the transmitter node 12 shall turn off when the transmitter node 12 is reset.

The housing 34 is preferably a water resistant or water proof enclosure. Furthermore, the housing 34 can be designed to withstand an impact and sized to be a pendant for wearing around a person's neck. As such, a pendant sized housing shall hold a coin sized cell battery. The housing shall open to permit the replacement of the battery. The pendant shall include at least one LED or other light source 37 to provide call assurance upon activation of at least one depressible button 26 and 28. The pendant shall include the ability to be worn as a necklace, with a wrist strap, on a belt or worn using similar methods and systems. In one exemplary embodiment, the housing 34 may be sized to be hand held.

The housing 34 may include a recessed speaker and a recessed microphone secured beneath a grill or other openings in the housing 30 that permit sound from the speaker and sound to the microphone. Optionally, additional buttons 28 may be found on the transmitter node 12. The microphone may be secured to the transmitter node 12 for transmitting an audio wave to the gateway node 10.

The receiver node 10 may output the message to a speaker or display device. In one embodiment, the receiver node 10 shall send a message to an end node transmitter node 12 as a result of receiving a message from a different transmitter node 12. The repeater is a 2.4 GHz radio sub-system which uses a synchronous channel hopping scheme which makes the system frequency agile. The entire sub-system will change channels every 3.5 seconds. The 2.4 GHz sub-system is synchronized and coordinated by the receiver node 10. A "Request-to-Send/Clear-To-Send" (RTS/CTS) protocol is used to coordinate the hopping of messages through repeaters. Multiple messages can be sent with each CTS response.

The receiver node 10 receives a call from at least one transmitter node 12 through the repeater 32. The system shall be scalable to accommodate additional nodes 12 preferably accomplished by using a jumper or setting a configuration bit when programming the units, or via a similar mechanism. The receiver node 10 may be configurable for receiving a message over a high speed link for uses such as turning on and off a light source accomplished through implementation of route based packets. The light source may include lights 38, 40 and 42 about the end node 36.

At least one repeater node 32 may be incorporated into the nurse call system 9 for extending the communications range between at least one gateway node 10 and at least one transmitter node 12. Each repeater node 32 shall be programmed to bridge between the 900 MHz network and 2.4 GHz high power network. Additionally, each repeater node 10 shall aggregate messages to lower bandwidth utilization.

The repeater node 32 includes a repeater network that is designed having at least two layers. The layers may include an inner layer and an outer layer. The layers are useful to route a message received from a transmitter node 12 between a plurality of repeater nodes 32 before subsequently delivering to the message the gateway node 10.

Figure 2:
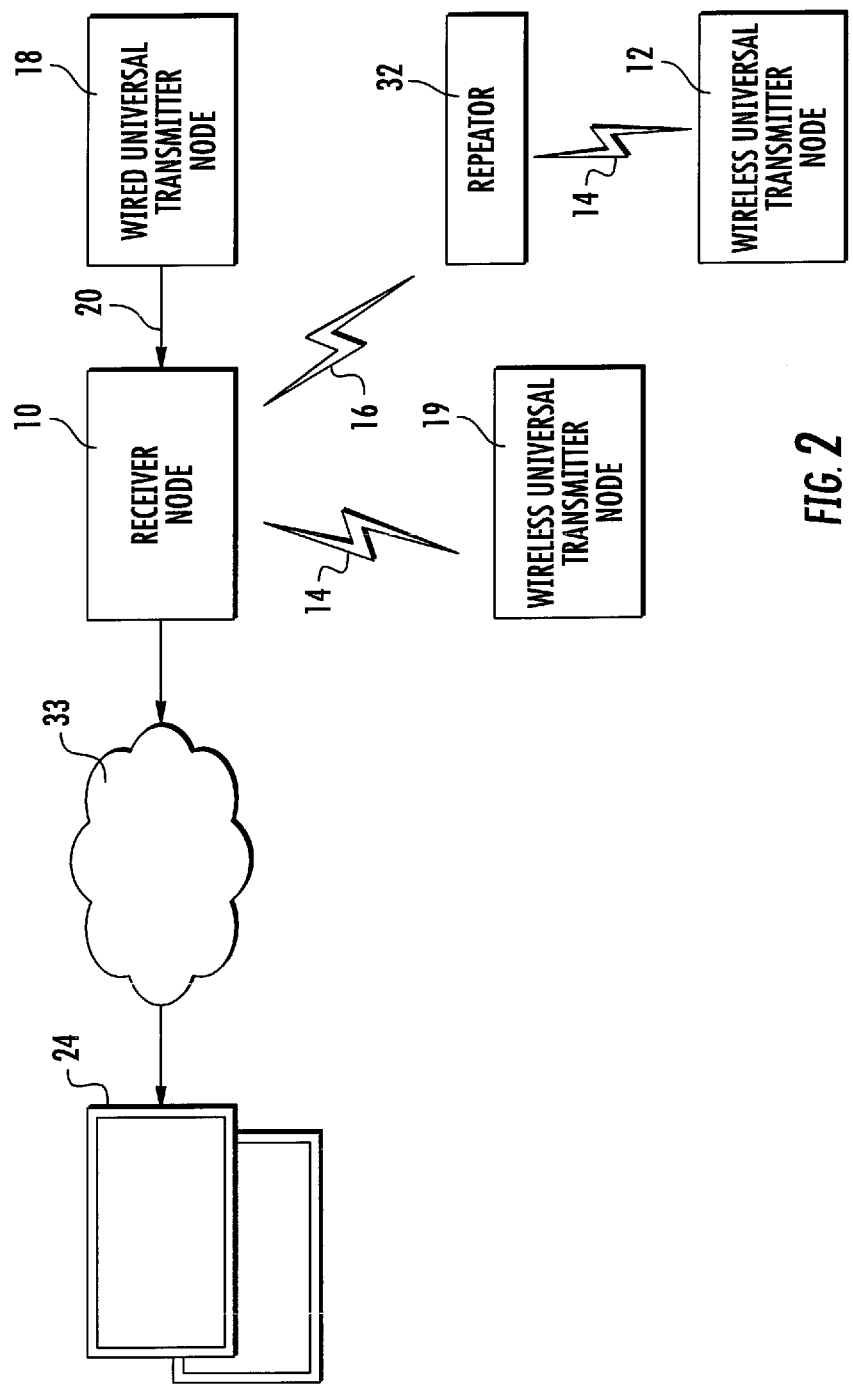
FIG. 2 is a block diagram of FIG. 1 further illustrating both a wired and wireless transmitter node.
Figure 3A:
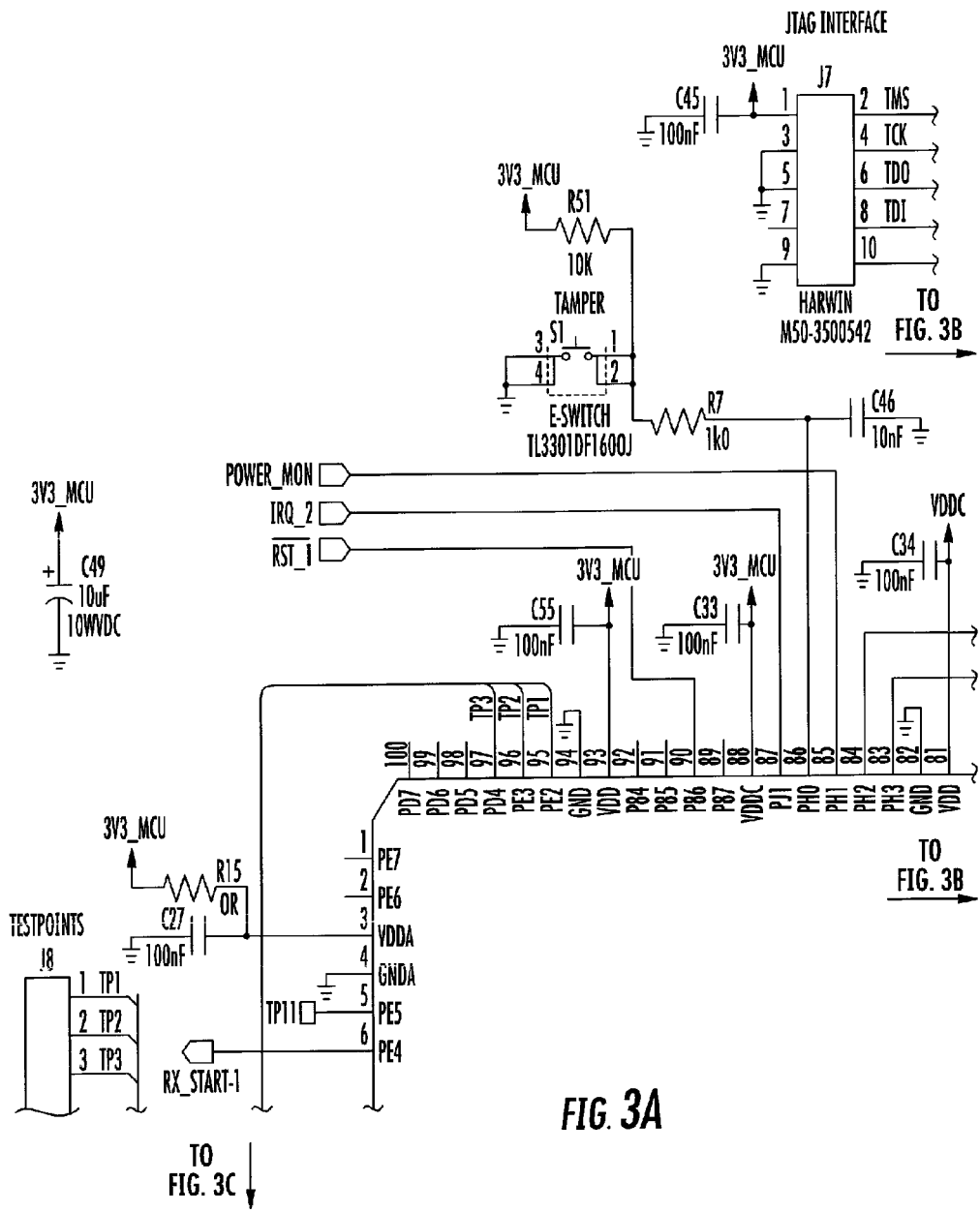
FIGS. 3A-3G illustrate a repeater circuit schematic.
Figure 3B:
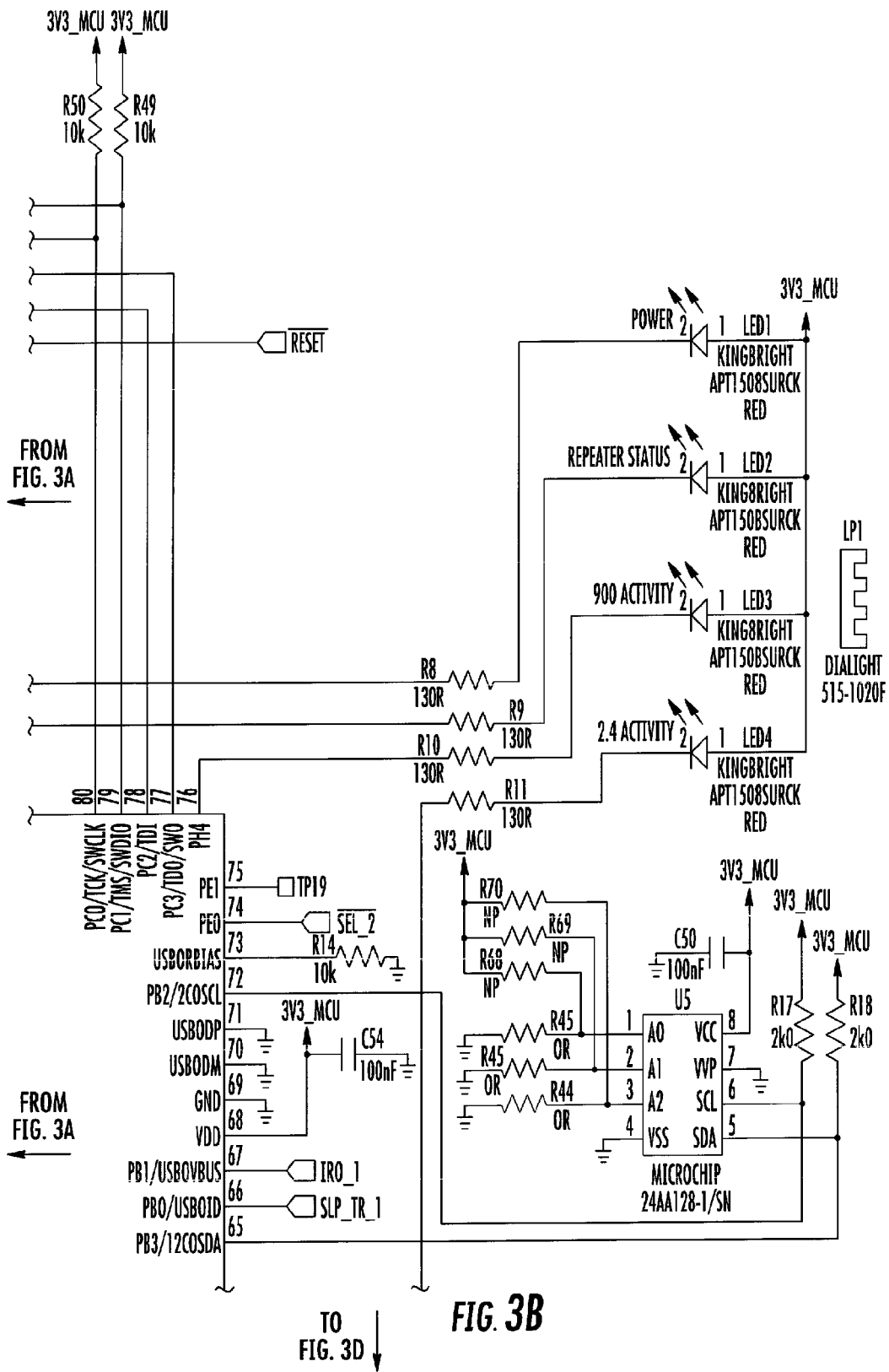
Figure 3C:
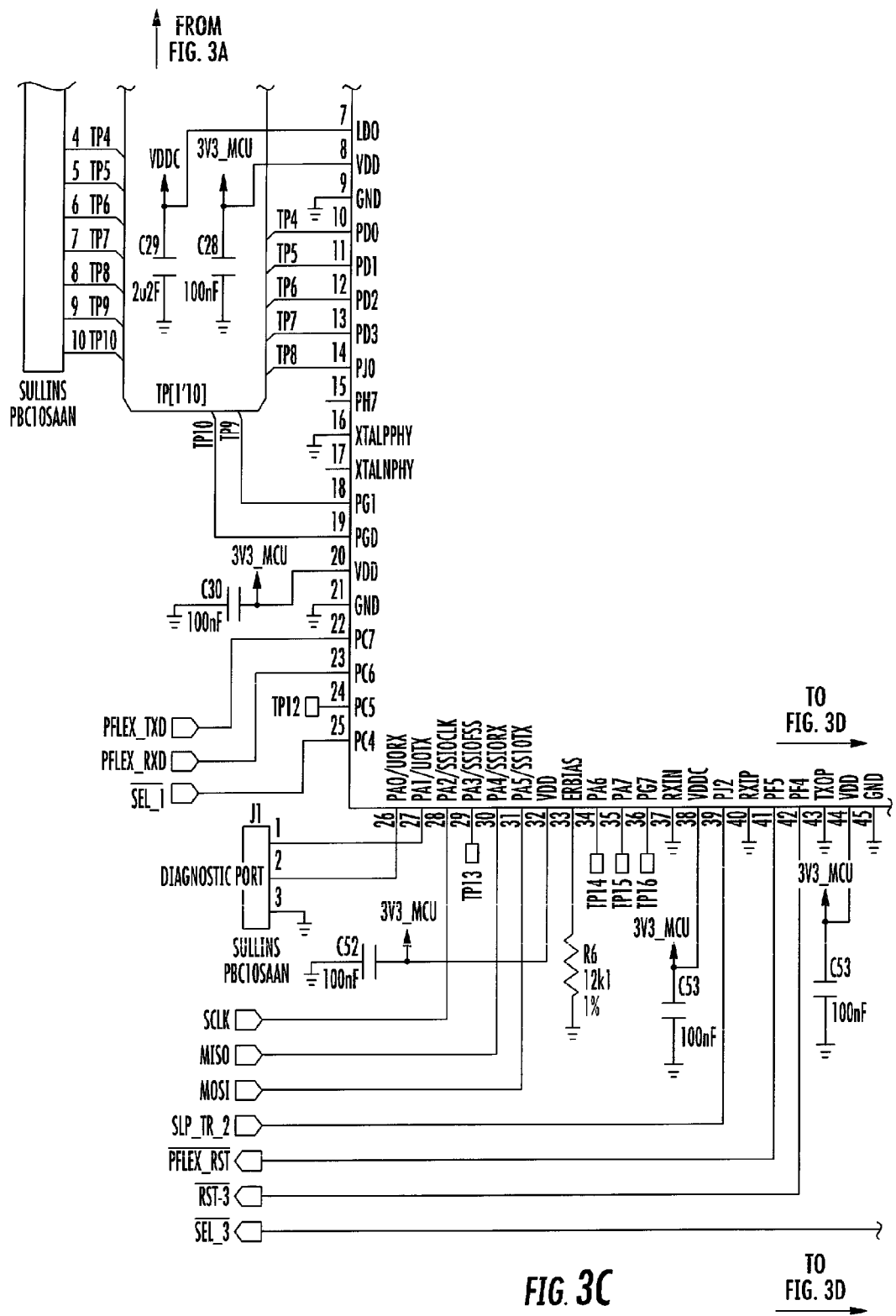
Figure 3D:
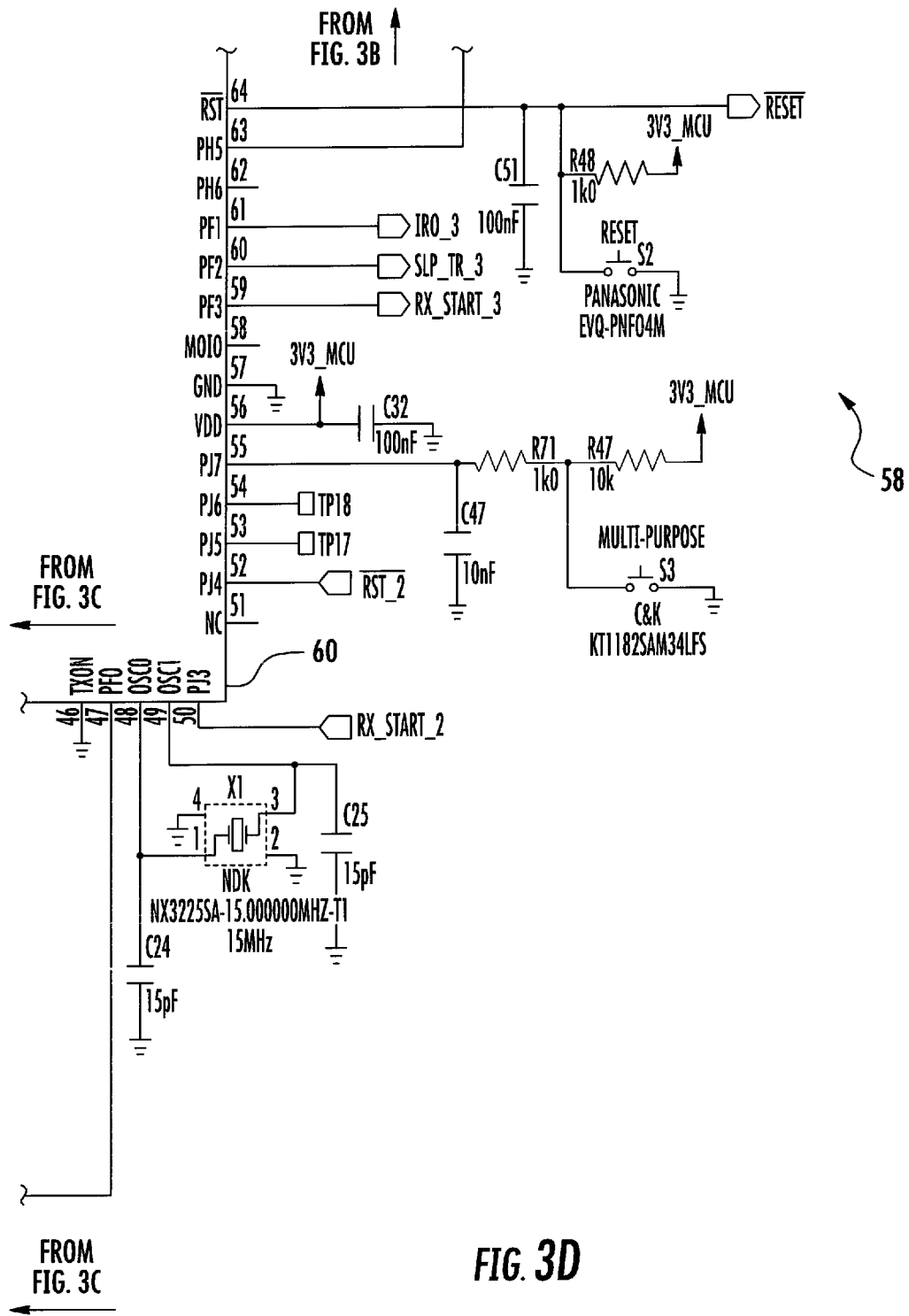
Figure 3E:
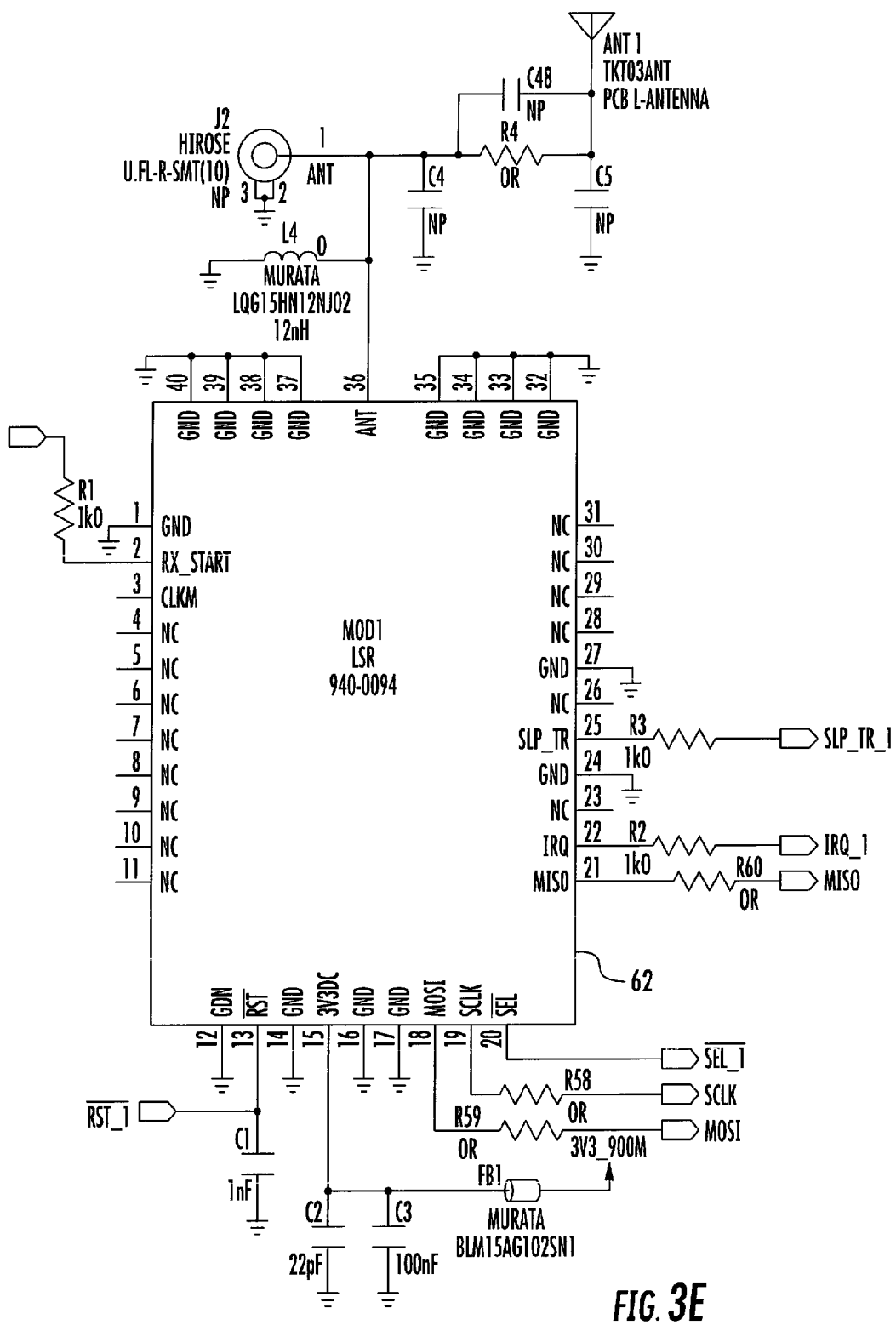
Figure 3F:
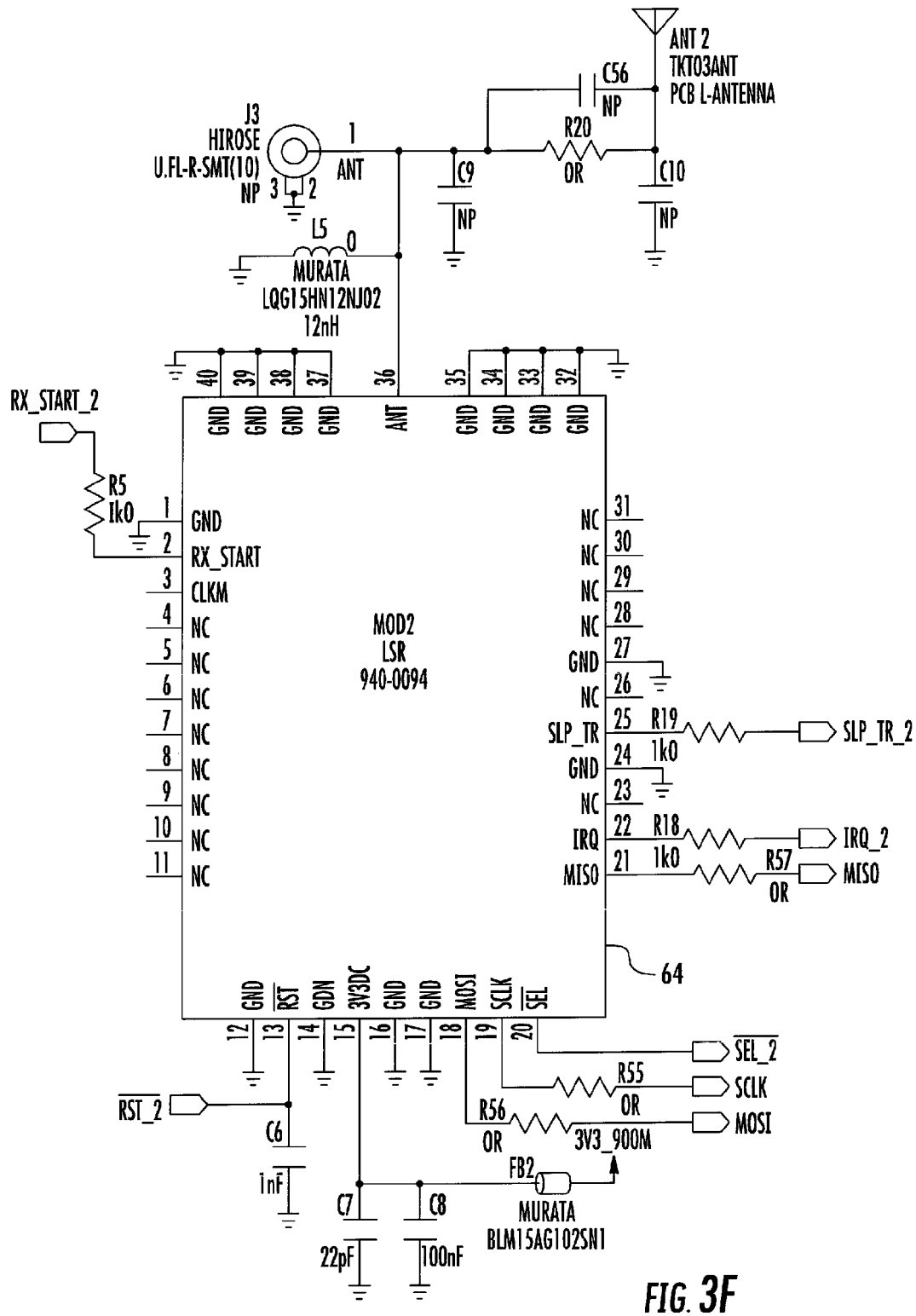
Figure 3G:
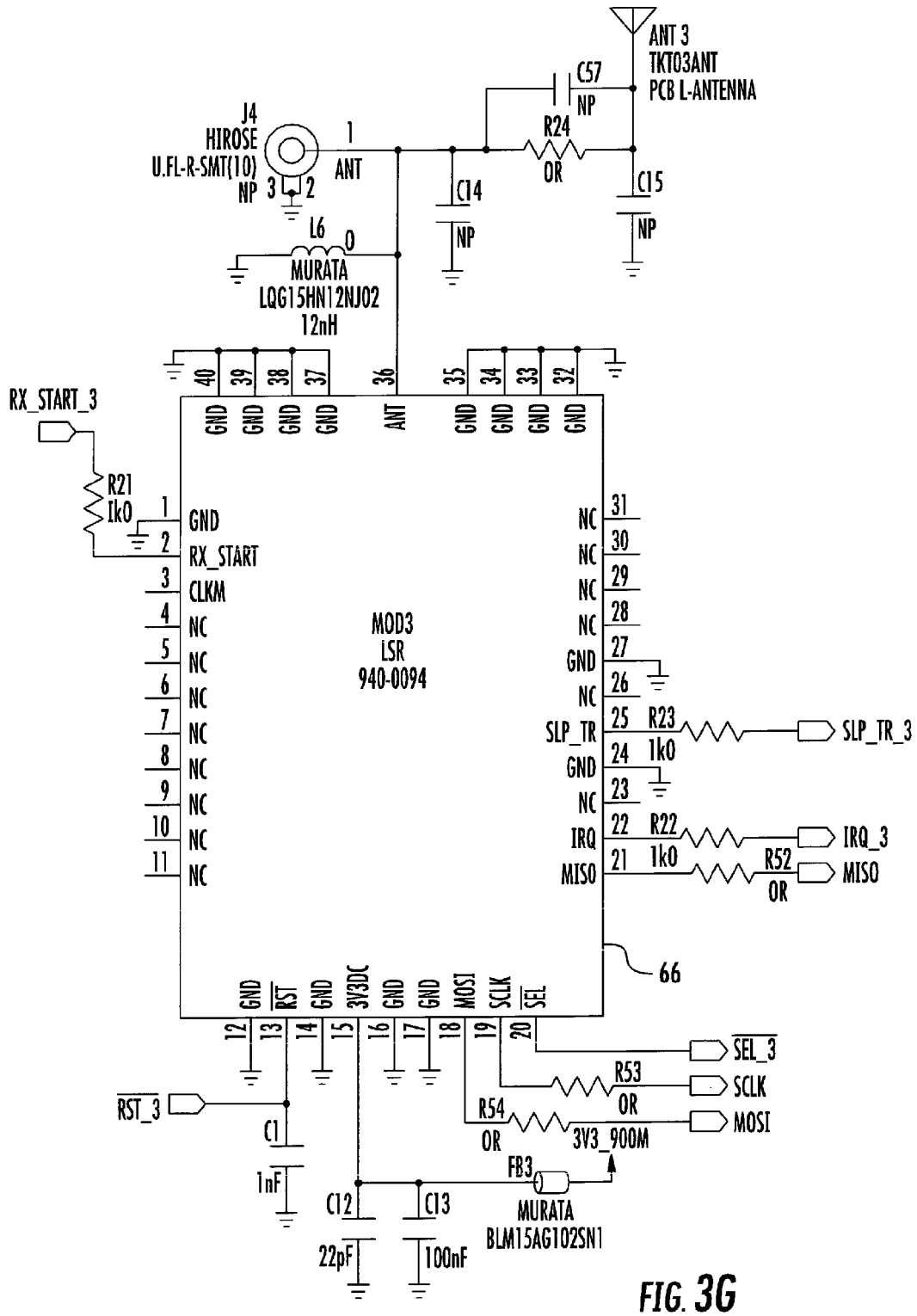

As shown in FIGS. 1 and 2, the receiver node routes a message to an end device, such as a computer module 24, an end node 36 and a transmitter node 12. The gateway link may couple to the end device by way of USB connection or other similar connections.

A user pushes at least one button 26 and 28 on a transmitter node 12 for assistance from a nurse or other medical staff member. Pressing against at least one button 26 and 28 on the transmitter node 12 shall transmit a signal to gateway node 10 and finally to at least one of a plurality an end nodes 36.

FIGS. 3A-3G depict a repeater circuit 58 with a 32-bit 80-MHz microprocessor 60 having a System Timer, integrated nested vectored interrupt controller, memory protection unit and a system control block electrically coupled to the 900 MHz receivers 62, 64, and 66. The receivers are a DSSS radio sub-system using an asynchronous frequency hopping. The identification signal received from the 900 MHz receivers is transmitted by the repeater circuit at 2.4 GHz.

Figure 4:
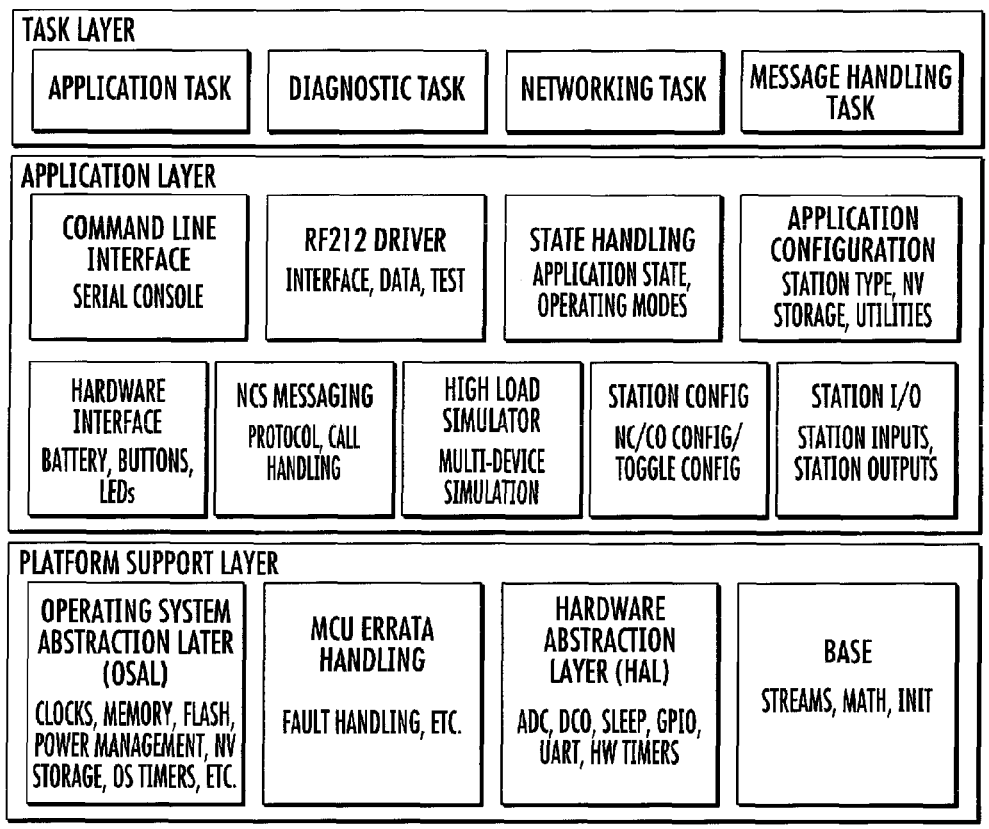
FIG. 4 is a block diagram depicting the three major layers of software defined with the universal device.
Figure 11:
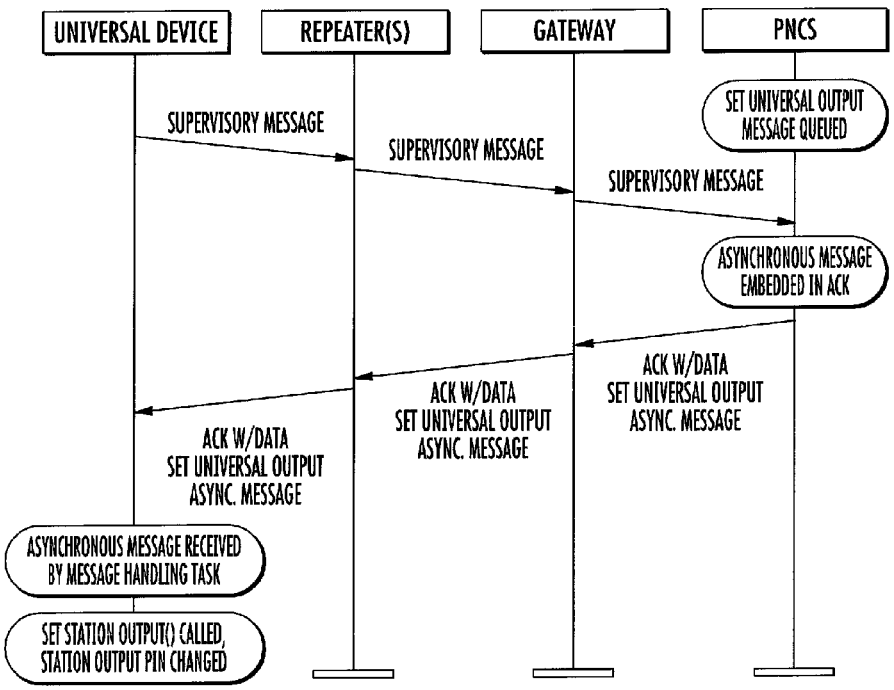
FIG. 11 is an example of an asynchronous message.

Referring now to FIG. 4, the block diagram indicates the three major layers of software defined within the universal device. The Layer defines four tasks; Application, Diagnostic, Networking and Message Handling. These tasks utilize the standard OSAL task design pattern and are configured to allow the MSP430 to enter Low Power Mode unless there is data to process. The Application Layer implements application specific functions called from the Task Layer. The Platform Support Layer implements the hardware interfaces and OSAL to support the Application and Task Layers.

The Application Task initializes non-volatile storage, configures initial GPIO states, initializes the hardware including the RF212 radio, starts application timers and kicks off the Application Tick timer. Once running, the Application Tick timer periodically wakes the MCU and updates the application state based on the current Operating Mode (see Operating Modes).

The Application Task is periodically triggered by an OSAL layer system tick timer through the APP_TIMER_EVENT. This timer has a configurable period (default 100 ms, assignable using SetApplicationTickPeriod( ) in Task_Application.c) and is required to maintain the application state machine through the APP_UPDATE_STATE_EVENT. This update interval determines the base rate for station input event handling (button presses in the case of pendants), battery monitoring rate and commissioning/registration/supervisory message transmission intervals. If code is added within the Application task, it should not run longer than the application tick period to avoid missed system tick timer events.

The RF212 radio driver (rf212*.c) must receive and process interrupts from the radio to transition between states and properly sequence incoming and outgoing data frames.

Figure 12:
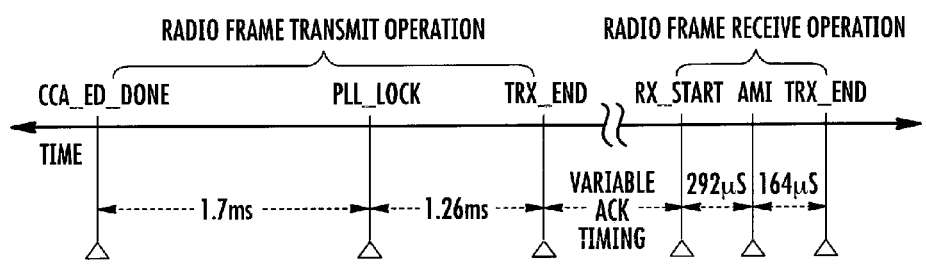
FIG. 12 depicts an interrupt timing diagram.

Radio interrupt handling is critical to ensure data frames are not lost. Upon receiving an IRQ from the radio, the MCU must immediately read the pending IRQ status register via the SPI bus to appropriately handle the request. Note that the timing between interrupts varies depending on frame size, PHY mode, ACK time, etc. FIG. 12 depicts a typical interrupt timing diagram for NCS protocol messaging.

The shortest timing between interrupts occurs between the AMI and TRX_END interrupts at approximately 164 pS. If interrupts are disabled for longer than 164 pS during a radio receive (i.e. an RX_START interrupt just occurred), the MCU can potentially miss the AMI interrupt if it isn't handled before the TRX_END interrupt comes in. This would result in a timeout waiting for the TRX_END interrupt and the frame would not be processed. Other scenarios where interrupts are disabled for long periods of time (e.g. for >292 pS just before an RX_START interrupt) can also cause frames to be dropped. FIG. 12 depicts a typical interrupt timing diagram for NCS protocol messaging.

The Diagnostic Task handles the diagnostic command line interface including processing commands from the serial console port.

The Networking Task handles sending/receiving NCS network messages and handles the communications with the radio transceiver over SRI. Incoming messages that require further processing are handed off to the Message Handling Task.

The Message Handling Task processes incoming asynchronous messages sent from a repeater within an ACK. This task handles the commissioning and registration process.

The Application layer contains application-specific functionality called by the Task Layer. This includes handling application state, application configuration, radio interface and input/output interfaces with external devices. Source files in this layer likely require customization for future software enhancements.

The Platform Support Layer contains standard software library files for HAL and OSAL support on the MSP430. In most cases, these files will not need to be modified. Discussion of this layer is kept to a minimum in this document but shown here for completeness.

The universal device operates in one of several Operating Modes. Referring to FIG. 5, the application state machine uses the Operating Mode to determine how certain events are processed. For example, in OMODE_TEST (System Test operating mode), supervisory messages are not sent to keep from interfering with manually driven commands/tests entered through the command line interface. The Operating Modes are illustrated in FIG. 5.

The universal device software is configured with basic default behavior for the input/output pins. This behavior can be further configured using the NC/NO Configand Toggle Configjumper blocks located on the device. This implementation provides for implementation of pushbuttons, door sensors, etc. for inputs and logic level switching for outputs. Nurse call station network messages (calls) are triggered from state changes on the input pins (rising/falling edges). FIG. 6 indicates the events (rising/falling edges) that trigger calls based on the configuration of the NC/NO Config and Toggle Config jumper block.

The NC/NO Configjumpers configure the NC/NO Config pins on the universal device. FIG. 7 provides a table of configuration for illustration. Pins are either internally pulled high (no jumper present) or tied to GND (jumper present). The NC/NO Config pins are defined in the station_config.h-file and are initialized with a call to initstationConfigin the station_config.cfile. Pin values are stored in the ncNoConfigStatesarray updated with a call to readStationConfig. The table below indicates the port bits as configured for each NC/NO Config pin. By default, these pins are configured by UD software to be internally pulled up by the MSP430 MCU (corresponding array entries contain '1'). If a jumper is present, the corresponding array entry will contain '0'. No interrupts are configured for these pins; they are configured to be polled when a state update is required.

Referring to FIG. 8, the Toggle Configjumpers configure the Toggle Config pins on the UD. Pins are either internally pulled high (no jumper present) or tied to GND (jumper present). The Toggle Config pins are defined in the station_config.hfile and are initialized with a call to initstationConfigin the station_config.cfile. Pin values are stored in the toggleConfigstatesarray updated with a call to readstationConfig. The table below indicates the port bits as configured for each Toggle Config pin. By default, these pins are configured by UD software to be internally pulled up by the MSP430 MCU (corresponding array entries contain '1'). If a jumper is present, the corresponding array entry will contain '0'. No interrupts are configured for these pins; they are configured to be polled when a state update is required.

The Station Output pins are defined by the station_outputs.hfile and are initialized with a call to initstationOutputs in the station_outputs.cfile. Pin values are stored in the outputstates array updated with a call to setstationOutput. FIG. 9 indicates the port bits as configured for each Station Output pin. By default, these pins are configured by UD software to be logic-low outputs (corresponding array entries contain '0').

Referring to FIG. 10, Station Input pins are defined by the station_inputs.hfile and are initialized with a call to initStationInputsin the station_inputs.cfile. Pin values are stored in the inputStates array updated with a call to readStationInputs. The table below indicates the port bits as configured for each station input pin. By default, these pins are configured by UD software to be internally pulled up by the MSP430 MCU (corresponding array entries contain '1'). On a contact closure to GND, the corresponding array entry changes from '1' to '0'. By default, interrupts are enabled for these pins, configured to trigger on both rising and falling edges.

Upon a state change of any of the input pins, the PORT2_ISR interrupt service routine is called in station_inputs.c. This routine is configured to clear the appropriate interrupt and setup a timer (usingTimer BI, CCR1, see Task_Application.cforTIMERB1_I5R definition) to occur 40 ms later providing a simple input de-bounce period.

After 40 ms, the readStationInputsfunction is called by TIMERB1_ISR. This function detects any state changes on the pins and queues input events to be handled by the ProcessStationInputs function called by the Application Task at its configured application timer tick interval. The Station_Input_Changed function is called to process the state change.

The Station_Input_Changed function is configured to display the state change to the diagnostic console, update states (e.g. tamper state) and optionally perform actions based on the currentOperating Mode (e.g. send a 'Universal Input' message to the radio). See the station_inputs.cfile for details.

For sending a message, by default the 'Tamper' input (Station Input Pin 2, P2.2) is configured as a normally closed input, sending an NCS Network message when either a rising or a falling edge is detected on its input pin. The message/call is placed with call_SendUniversalInput from within station_inputs.c. The standard calls the UD is capable of sending are defined in call.c. The functions in call.c create and queue up packets to the Networking Task and send a message to initiate the transmit operation.

When receiving a message, by default the 'Station Outputs' can be switched to logic low/high from the PNCS via asynchronous messaging. This operation requires the universal device to send a supervisory message (or other message with an ACK format supporting asynchronous messaging, see 900 MHz Message Definitions) in order to receive a downstream 'Universal Output' asynchronous message. An example of this sequence is shown if FIG. 10.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A dual band nurse call system comprising:
    at least one transmitter assembly to be carried by a health care patient wherein said transmitter is a 900 MHz DSSS radio sub-system using asynchronous frequency hopping, said transmitter providing a transmitter identification signal at 900 MHz;
    at least one locator assembly constructed and arranged to receive said identification signal at 900 MHz,
    at least one repeater assembly constructed and arranged to receive said identification signal at 900 MHz and transmit said identification signal at 2.4 GHz;
    a gateway assembly constructed and arranged to receive said identification signal at 2.4 GHz and forward said identification signal to at least one receiver node for distribution;
    a network control software constructed and arranged to operate in a plurality of modes to determine network events, said network control software communicates with said nurse call system at 900 MH and operates as a generic interface that controls communication between said repeater, said gateway, said locator and said receiving node.

2. The dual band nurse call system according to claim 1 wherein each said transmitter implements a Carrier Sense Multiple Access protocol.

3. The dual band nurse call system according to claim 1 wherein said repeater implements a Carrier Sense Multiple Access protocol.

4. The dual band nurse call system according to claim 1 wherein said repeater receiving identification signals will aggregate said signals together through said microprocessor before forwarding to said gateway link.

5. The dual band nurse call system according to claim 1 wherein said identification signal is an audible warning sound and said identification signal is audibly outputted to a central station.

6. The dual band nurse call system according to claim 5 wherein said audible warning is a voice.

7. The dual band nurse call system according to claim 1 wherein said identification signal is an audible warning sound and said identification signal is visually outputted to a central station.

8. The dual band nurse call system according to claim 1 wherein said transmitter enters a low power mode when not communicating and said repeater periodically polling said transmitter.

9. The dual band nurse call system according to claim 1 including an end node constructed and arranged to alert a health care employee of a transmitter identification signal.

10. The dual band nurse call system according to claim 9 wherein said end node is a route based packet communication deliverable over a high speed link.

11. The dual band nurse call system according to claim 10 wherein said packet communication is used to activate a switch.

12. The dual band nurse call system according to claim 1 wherein said repeater will automatically change frequencies to mitigate potential radio interference.

13. The dual band nurse call system according to claim 1 wherein said transmitter is a pendant having at least two depressible buttons, whereby depression of either said buttons will transmit a discrete identification signal.

14. The dual band nurse call system according to claim 1 wherein said universal device software is configured with default behaviors for input/output pins.

15. A dual band nurse call system comprising:
- at least one transmitter assembly to be carried by a health care patient, said transmitter providing a transmitter identification signal using a DSSS radio sub-system at 900 MHz using an asynchronous frequency hopping;
- at least one locator assembly constructed and arranged to receive said identification signal at 900 MHz,
- at least one repeater assembly constructed and arranged to receive said identification signal at 900 MHz and transmit said identification signal at 2.4 GHz, said repeater will automatically change frequencies to mitigate potential radio interference;
- a gateway assembly constructed and arranged to receive said identification signal at 2.4 GHz and forward said identification signal to at least one receiver node for distribution;
- a network control software constructed and arranged to operate in a plurality of modes to determine network events, said network control software communicates with said nurse call system at 900 MH and operates as a generic interface that controls communication between said repeater, said gateway, said locator and said receiving node;
- said transmitter enters a low power mode when not communicating and said repeater periodically polling said transmitter.

16. The dual band nurse call system according to claim 15 wherein each said transmitter implements a Carrier Sense Multiple Access protocol.

17. The dual band nurse call system according to claim 15 wherein said repeater implements a Carrier Sense Multiple Access protocol.

18. The dual band nurse call system according to claim 15 wherein said transmitter is a pendant having at least two depressible buttons, whereby depression of either said buttons will transmit a discrete identification signal.

* * * * *